United States Patent
Yang et al.

(10) Patent No.: US 8,257,272 B2
(45) Date of Patent: Sep. 4, 2012

(54) IMPLANTABLE SENSOR FOR MEASURING PHYSIOLOGIC INFORMATION

(75) Inventors: Michael Yang, Thousand Oaks, CA (US); Wenbo Hou, Lancaster, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/018,631

(22) Filed: Feb. 1, 2011

(65) Prior Publication Data

US 2011/0137187 A1    Jun. 9, 2011

Related U.S. Application Data

(63) Continuation of application No. 11/750,226, filed on May 17, 2007, now Pat. No. 7,901,360.

(51) Int. Cl.
*A61B 5/0295* (2006.01)

(52) U.S. Cl. ............................. 600/508; 607/119

(58) Field of Classification Search ............. None
See application file for complete search history.

(56) References Cited

U.S. PATENT DOCUMENTS

| | | | |
|---|---|---|---|
| 4,634,917 A | 1/1987 | Dvorsky et al. | |
| 4,868,447 A | 9/1989 | Lee et al. | |
| 5,261,418 A | 11/1993 | Ferek-Petric | |
| 5,496,361 A | 3/1996 | Moberg et al. | |
| 5,628,777 A | 5/1997 | Moberg et al. | |
| 5,833,713 A | 11/1998 | Moberg | |
| 6,246,895 B1 | 6/2001 | Plewes | |
| 6,246,898 B1 | 6/2001 | Vesely et al. | |
| 6,540,699 B1 | 4/2003 | Smith | |
| 6,829,507 B1 | 12/2004 | Lidman et al. | |
| 6,918,870 B1 | 7/2005 | Hunyor et al. | |
| 2003/0032998 A1* | 2/2003 | Altman | 607/120 |
| 2003/0060674 A1 | 3/2003 | Gifford, III et al. | |
| 2003/0158494 A1* | 8/2003 | Dahl et al. | 600/526 |
| 2004/0068203 A1* | 4/2004 | Gellman et al. | 600/587 |
| 2004/0133092 A1 | 7/2004 | Kain | |
| 2004/0172078 A1 | 9/2004 | Chinchoy | |
| 2005/0102026 A1 | 5/2005 | Turner et al. | |
| 2006/0107749 A1 | 5/2006 | Liu et al. | |
| 2007/0049977 A1* | 3/2007 | Von Arx et al. | 607/9 |
| 2007/0232849 A1* | 10/2007 | Gertner | 600/37 |

FOREIGN PATENT DOCUMENTS

| | | |
|---|---|---|
| WO | 9503086 | 2/1995 |
| WO | 9503086 A3 | 2/1995 |

OTHER PUBLICATIONS

NonFinal Office Action, mailed Jun. 2, 2010—U.S. Appl. No. 11/750,226.
Final Office Action, mailed Oct. 8, 2010—U.S. Appl. No. 11/750,226.
Notice of Allowance, mailed Dec. 10, 2010—U.S. Appl. No. 11/750,226.

* cited by examiner

*Primary Examiner* — Carl H Layno
*Assistant Examiner* — Paula J Stice

(57) ABSTRACT

An implantable sensor is provided that includes a piezopolymer sensor element including a body having a plurality of layers of a piezopolymer, and an attachment device configured to hold the piezopolymer sensor element in direct contact with at least one of a bodily fluid and bodily tissue such that the piezopolymer sensor element is configured to bend in response to motion of the at least one of bodily fluid and bodily tissue. A pair of electrodes is attached to the piezopolymer sensor element and the electrodes are configured to collect an electrical charge that is generated within the piezopolymer sensor element due to the bending of the piezopolymer sensor element.

12 Claims, 9 Drawing Sheets

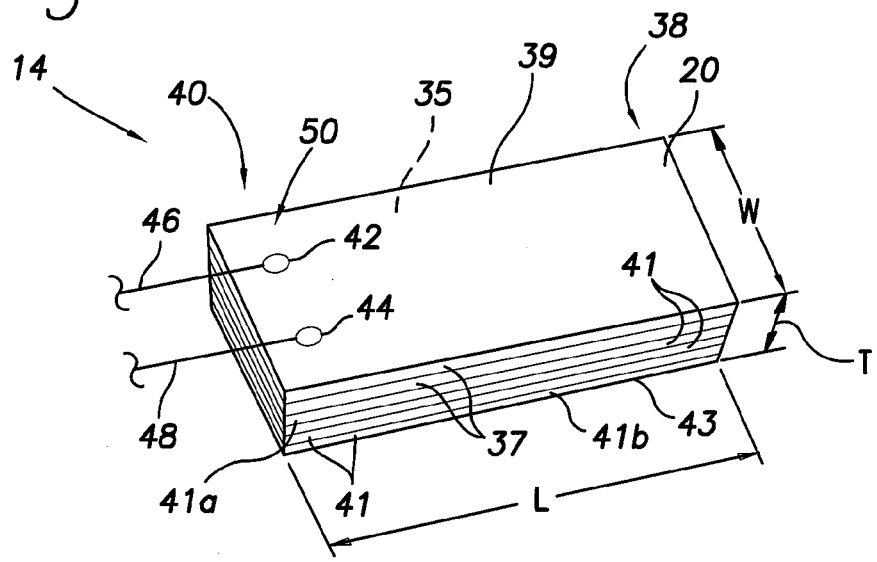
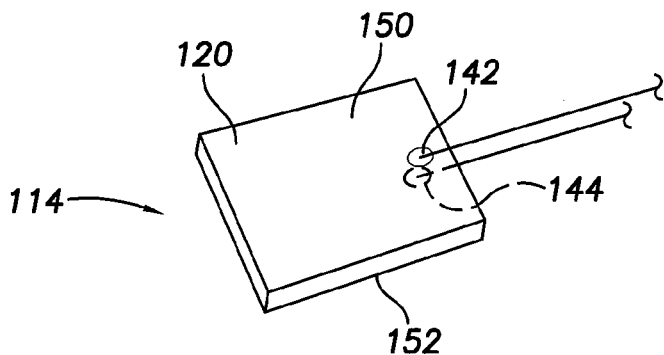
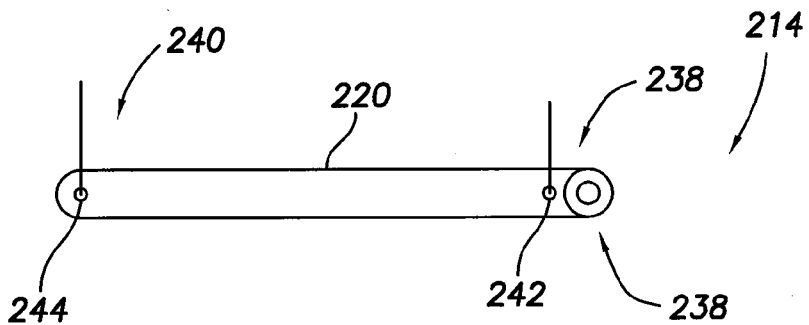

IMPLANTABLE SENSOR FOR MEASURING PHYSIOLOGIC INFORMATION

CROSS REFERENCE TO RELATED APPLICATIONS

This application is a continuation of U.S. patent application Ser. No. 11/750,226, filed May 17, 2007, titled "Implantable Sensor for Measuring Physiologic Information," now U.S. Pat. No. 7,901,360.

FIELD OF THE INVENTION

Embodiments of the present invention pertain generally to methods and systems for measuring cardiac-related physiologic information utilizing an implantable sensor, for example, for the treatment and/or diagnosis of congestive heart failure.

BACKGROUND OF THE INVENTION

In the United States, it is estimated that approximately five million people have congestive heart failure (CHF). During treatment of some CHF patients, the contractility of the heart may be assessed for diagnosis and/or treatment purposes. In addition to being useful for generally monitoring the progression of a patient's cardiac disease, the heart's contractility may be monitored over time to monitor the patient's response to therapy and make any appropriate changes thereto. For example, some patients suffering from CHF have an abnormality in the electrical conducting system of the heart, sometimes referred to as "intraventricular conduction delay" or "bundle branch block" that causes the left and right ventricles to beat out of phase instead of simultaneously. Cardiac resynchronization therapy (CRT), sometimes referred to as "biventricular pacing", may be used to re-coordinate the beating of the left and right ventricles by pacing both ventricles simultaneously. In contrast to CRT, conventional pacemakers typically only pace the right ventricle. During treatment of CRT patients, the systolic and diastolic pump properties of one or both of the ventricles may be assessed to assist pacing the ventricles and/or monitoring the heart's contractility over time.

Some known methods of assessing the heart's contractility include introducing a conventional blood pressure or pressure-volume loop transducer into the ventricle chamber from the femoral artery to determine the ventricular blood pressure and volume. However, such transducers are typically removed after each measurement because the presence of the transducer and associated components within the left ventricle risk causing a stroke. Accordingly, conventional transducers are generally not implantable within the left ventricle for continuously monitoring heart contractility over time. Medical imaging, such as echo imaging or magnetic resonance imaging (MIR), can be used to non-invasively measure ventricular blood pressure. However, medical imaging procedures are typically lengthy and expensive, and therefore may not be suitable for monitoring cardiac contractility over time because of the cost and/or inconvenience of the multiple of procedures to the patient.

Conventional diaphragm-type sensors (force gauges) may be implantable within the ventricles or within the pericardial space adjacent the ventricles for continuously monitoring contractility over time. However, conventional diaphragm-type sensors may need to be hermetically sealed to operate within the human body, and are typically battery-powered. Conventional diaphragm-type sensors may therefore be bulkier and/or less reliable than is desired for implantation within or adjacent to the heart. Moreover, the battery may limit the duration for which conventional diaphragm-type sensors may remain operable within the human body without being serviced or replaced.

Sensors fabricated from lead zirconate titnate (PZT), a piezoelectric ceramic material, have been contemplated for use as an implantable sensor that measures heart contractility. However, because PZT has a relatively large $d_{33}$ coefficient, PZT sensors are typically sensitive to hydrostatic pressure and sound waves. Specifically, hydrostatic pressure and/or sound waves may cause the PZT sensor to respond to movement in a direction approximately parallel to a thickness of the PZT sensor. The response caused by such movement may add undesirable noise to the measurement signal of the PZT sensor that represents the motion of the heart, thereby reducing an overall signal clarity of heart contractility information. The relatively large d33 coefficient of PZT causes PZT to be sensitive to triboelectric charges generated within the PZT sensor by friction between the PZT sensor and surfaces with which the PZT sensor is in contact, thereby further reducing signal clarity of the heart contractility information. Moreover, because PZT contains lead, PZT may not be biocompatible and therefore not be suitable for implantation within the human body.

A need remains for an implantable sensor that is directed to overcoming one or more of the problems set forth above. A need remains for an implantable sensor with improved signal clarity that is biocompatible and does not require an external power source and/or hermetic sealing.

SUMMARY

In one embodiment, an implantable sensor is provided that includes a piezopolymer sensor element including a body having a plurality of layers of a piezopolymer, and an attachment device configured to hold the piezopolymer sensor element in direct contact with at least one of a bodily fluid and bodily tissue such that the piezopolymer sensor element is configured to bend in response to motion of the at least one of bodily fluid and bodily tissue. A pair of electrodes are attached to the piezopolymer sensor element and the electrodes are configured to collect an electrical charge that is generated within the piezopolymer sensor element due to the bending of the piezopolymer sensor element.

Optionally, the piezopolymer sensor element may include polyvinylidene fluoride (PVDF). In some embodiments, the piezopolymer sensor element may be a first piezopolymer sensor element, and the implantable sensor may further include a second piezopolymer sensor element held by the attachment device or another attachment device. The first and second piezopolymer sensor elements may be held in a desired orientation with respect to one another such that the second piezopolymer sensor element bends in a direction arranged approximately perpendicular to the first piezopolymer sensor element. In some embodiments, the attachment device is configured to hold the piezopolymer sensor element in direct contact with blood flowing through a ventricle of the heart. The attachment device may be configured, in some embodiments, to hold the piezopolymer sensor element in direct contact with an epicardial surface of the heart, an endocardial surface of the heart, and/or a surface of a pericardium. A radio-frequency (RF) transmitter may optionally be electrically connected to the electrodes for transmitting an electrical voltage output of the electrodes.

In another embodiment, a method is provided for measuring the motion of a heart. The method includes positioning a sensor element within a pericardial space of a pericardium of the heart in contact with at least one of bodily tissue and bodily fluid such that the sensor element bends in response to motion of the at least one of bodily tissue and bodily fluid, measuring an output voltage of electrical charges generated on at least one surface of the sensor element due to the bending of the sensor element, and determining a bending moment of the sensor element based on the measured output voltage.

BRIEF DESCRIPTION OF THE DRAWINGS

FIG. 3 illustrates the sensor element of the system shown in FIGS. 1 and 2 formed in accordance with an embodiment of the present invention.

FIG. 5 illustrates a sensor element formed in accordance with an alternative embodiment of the present invention.

FIG. 6 illustrates a sensor element formed in accordance with another alternative embodiment of the present invention.

DETAILED DESCRIPTION OF THE INVENTION

Figure 1:
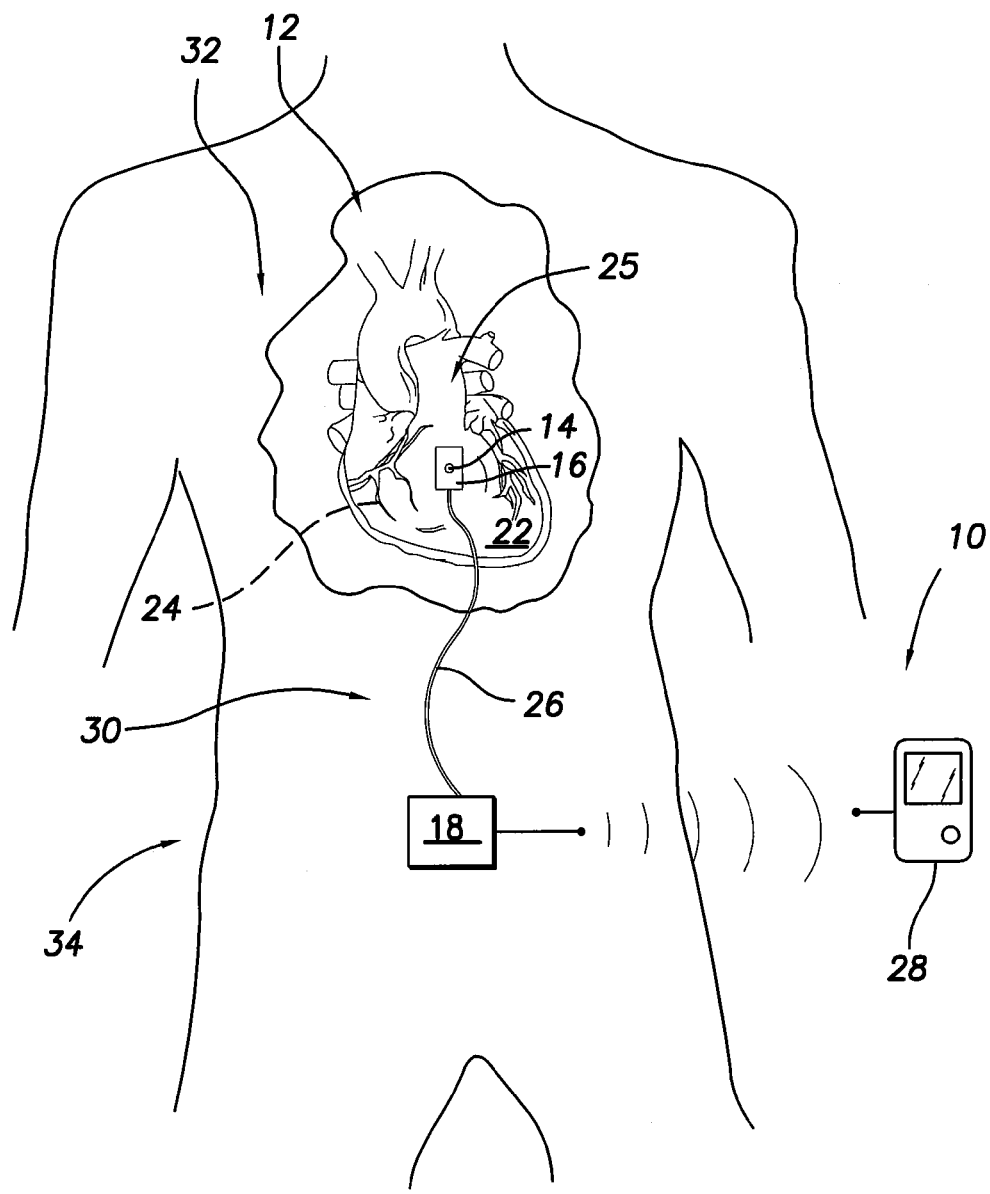
FIG. 1 illustrates an implantable sensor system formed in accordance with an embodiment of the present invention.

FIG. 1 illustrates an implantable sensor system 10 formed in accordance with an embodiment of the present invention. The sensor system 10 may be used, for example, for generally monitoring the contractility of a patient's heart 12, e.g., monitoring the diastolic and systolic pump properties of one or both of the ventricles of the heart. The system 10 includes a sensor element 14, an attachment device 16 for positioning the sensor element in direct contact with bodily tissue and/or bodily fluid, and a processing unit 18. The sensor element 14 is fabricated using a "piezopolymer", which as used herein is intended to mean a polymer having piezoelectric properties. The sensor element 14 may be fabricated from any suitable piezopolymer(s) that enables the sensor element 14 to function as described herein, such as, but not limited to, polyvinylidene fluoride (PVDF).

As will be described in more detail below, the sensor element 14 bends in response to motion of the bodily tissue and/or bodily fluid. As the sensor element bends, an electrical charge is generated within a body 20 (FIG. 3) of the sensor element 14. A voltage of the electrical charge is proportional to the bending moment of the sensor element 14, which can be used to determine motion properties of the fluid and/or tissue whose motion caused the sensor element to bend. In some embodiments, two sensor elements 14 may be held, whether by the same or a different attachment device 16, in a desired orientation with respect to one another such that the two sensor elements bend in directions arranged approximately perpendicular to each other (e.g., the sensor elements 614 and 714, shown in FIG. 10, and the pair of sensor elements 14 shown in FIG. 12).

In the exemplary embodiments, the sensor element 14 is positioned within and/or adjacent the heart 12 for obtaining contractility information about the heart, e.g., for measuring diastolic and systolic pump properties of the heart. However, the sensor system 10 is not limited to use with the heart 12, but rather may be used to measure the motion of any bodily tissue and/or bodily fluid, such as, but not limited to, joints, the lungs, and/or other muscles within the body besides the heart. When used to measure the contractility of the heart 12, the sensor element 14 may be positioned anywhere within, on, and/or adjacent the heart that is suitable for measuring motion of the heart itself and/or blood being pumped through the heart. For example, the sensor element 14 may be positioned in the pericardial space in direct contact with an epicardial, or external surface of the heart 12, as is shown in FIG. 1 wherein the sensor element 14 is positioned on an epicardial surface 22 of a left ventricle 25 of the heart. The sensor element 14 may also be positioned in direct contact with an endocardial, or internal, surface of the heart 12, e.g., an endocardial surface 24 of the left ventricle 25.

Positioning the sensor element 14 in direct contact with a surface of the heart 12 enables direct measurement of the motion of the surface. Alternatively, the sensor element 14 may not be positioned in direct contact with a surface of the heart 12, but rather may be positioned in direct contact with other bodily tissue that is adjacent to, or in direct contact with, a surface of the heart 12. For example, the sensor element 14 may be positioned within a pericardial space 13 (FIG. 2) in direct contact with a surface of the pericardium 15 (FIG. 2), e.g., the surface 17 (FIG. 2) of a serous pericardium 19 (FIG. 2) of the pericardium and/or a surface 21 (FIG. 2) of a fibrous pericardium 23 of the pericardium.

The sensor element 14 may also be positioned to indirectly measure the motion of the heart by measuring other properties that relate to, and can be used to determine, motion. For example, the sensor element 14 can be positioned within the heart 12 in direct contact with a flow path of blood through the heart. Contractility information about the heart 12 can then be determined based on the motion of blood through the heart. One example of measuring blood flow includes positioning the sensor element 14 within a ventricle (e.g., the left ventricle 25) of the heart 12 in direct contact with blood flowing through the ventricle to measure blood flow therethrough. The sensor element 14 may also be positioned on, adjacent, and/or within vessels leading into and out of the heart 12 (e.g., the aorta) to obtain contractility information about the heart.

The attachment device 16 may include any suitable structures, elements, components, configurations, arrangements, and/or geometries that securely positions and holds the sensor element 14 in the positions (e.g., location and/or orientation) described and/or illustrated herein. The attachment device 16 may form a portion of a lead, as shown in FIG. 1 with respect to the lead 26. Alternatively, the attachment device 16 may not form a portion of, and/or may not be connected to, a lead. Various examples of attachment devices are described below with respect to FIGS. 8-11.

The position of the sensor element 14 may be selected anywhere within, on, and/or adjacent the heart 12 to determine contractility information of the heart overall and/or at specific locations adjacent the sensor element 14. In some embodiments, to provide more comprehensive contractility information, a plurality of sensor elements 14 (whether part of the same lead or whether connected to the same RF transmitter) may be positioned at different locations within, on, and/or adjacent the heart 12 and/or at different orientations with respect to other sensor elements. For example, because motion of the heart 12 is generally not linear, it may be desirable to position a pair of sensor elements 14 as oriented approximately perpendicular to each other such that the pair of sensor elements each bend in a direction arranged approximately perpendicularly to each other (e.g., for measuring both short and long axis motion of heart 12).

Generally, the contractility of the heart is assessed using the sensor system 10 for diagnosis and/or treatment of the patient. In addition to being useful for generally monitoring the progression of a patient's cardiac disease, contractility of the heart may be monitored over time to monitor the patient's response to therapy and make any appropriate changes thereto. For example, the contractility information obtained by the sensor system 10 may provide a physician with information as to whether the hemodynamic functioning of a patient has improved, how scar formation is progressing, the status of local or global heart failure, and/or the like. The contractility information may also be used in combination with other systems to control functions of such other systems. For example, the contractility information may be used by, but is not limited to being used by, another system (not shown), such as, but not limited to, a pulse generator, a pacemaker, an implantable cardioverter defibrillator, a defibrillator, a therapy delivery module that paces and/or provides electrical stimulation to the heart 12, and/or the like to, for example, control an appropriate pacing scheme or defibrillation event. One example of a specific use for the sensor system 10 is for determining the least contraction site of the heart 12 where a pacing electrode (not shown) can be positioned for optimal pacing. External systems (not shown), such as, but not limited to, an external health monitoring system at a treatment facility and/or the patient's home may also make use of the contractility information for treatment and/or diagnosis purposes.

Voltage measurement signals from the sensor element 14 are provided to the processing unit 18 via an electrical connection therebetween. The sensor element 14 may be electrically connected to the processing unit 18 through a lead 26, as is shown in FIG. 1. Optionally, the sensor element 14 may be incorporated into the lead of another system (not shown), such as, but not limited to a pulse generator, a pacemaker, an implantable cardioverter defibrillator, a defibrillator, a therapy delivery module that paces and/or provides electrical stimulation to the heart 12, and/or the like. Additionally or alternatively to a lead, the sensor element 14 may be electrically connected to the processing unit 18 using a wireless connection, such as, but not limited to, using an RF transmitter 36 (FIG. 2) electrically connected to the sensor element 14.

The processing unit 18 may process the voltage measurement signals received from the sensor element 14 to determine the bending moment represented by each of the signals. The processing unit 18 may further process the bending moments to determine contractility information of the heart 12 or portions thereof, e.g., the systolic and/or diastolic pump properties of one or both of the ventricles. The processing unit 18 includes a memory (not shown) for storing the voltage measurement signals received from the sensor element 14, as well as for storing any determined bending moments, any determined contractility information, and/or other information relevant to treatment and/or diagnosis of the patient.

The processing unit 18 communicates with an external system 28, such as, but not limited to, an external health monitoring system at a treatment facility and/or the patient's home, and/or a laptop, handheld, or desktop computer at the treatment facility. The processing unit 18 may communicate any determined contractility and/or other relevant information to the external system 28 for use by the external system 28 and/or a physician in diagnosing, treating, and/or monitoring the patient. Additionally or alternatively, the external system 28 may determine contractility information of the heart by processing voltage measurement signals, any determined bending moments, and/or other relevant information received from the processing unit 18. The processing unit 18 may communicate with the external system 28 using a wireless connection (as shown in FIG. 1) and/or wired connection.

The processing unit 18 may also cooperate with other systems implanted within the patient's body to make use of the contractility information obtained by the sensor system 10, as is described above. For example, the processing unit 18 may optionally communicate with, constitute the processing unit of, or be incorporated into another system (not shown) implanted within the patient's body, such as, but not limited to a pulse generator, a pacemaker, an implantable cardioverter defibrillator, a defibrillator, a therapy delivery module that paces and/or provides electrical stimulation to the heart 12, and/or the like.

The processing unit 18 may be implanted at any suitable location within the body that enables it to function as described herein, such as, but not limited to, in the abdomen 30 (as shown in FIG. 1) or a pectoral muscle 32. Alternatively, the processing unit 18 may be positioned externally to the patient's body. For example, the processing unit 18 may be worn externally on the patient's hip 34 or another body portion, or may remain at a treatment facility and be connected (e.g., via a lead or wirelessly) to the sensor element 14 when the patient comes to the facility for treatment.

Figure 2:
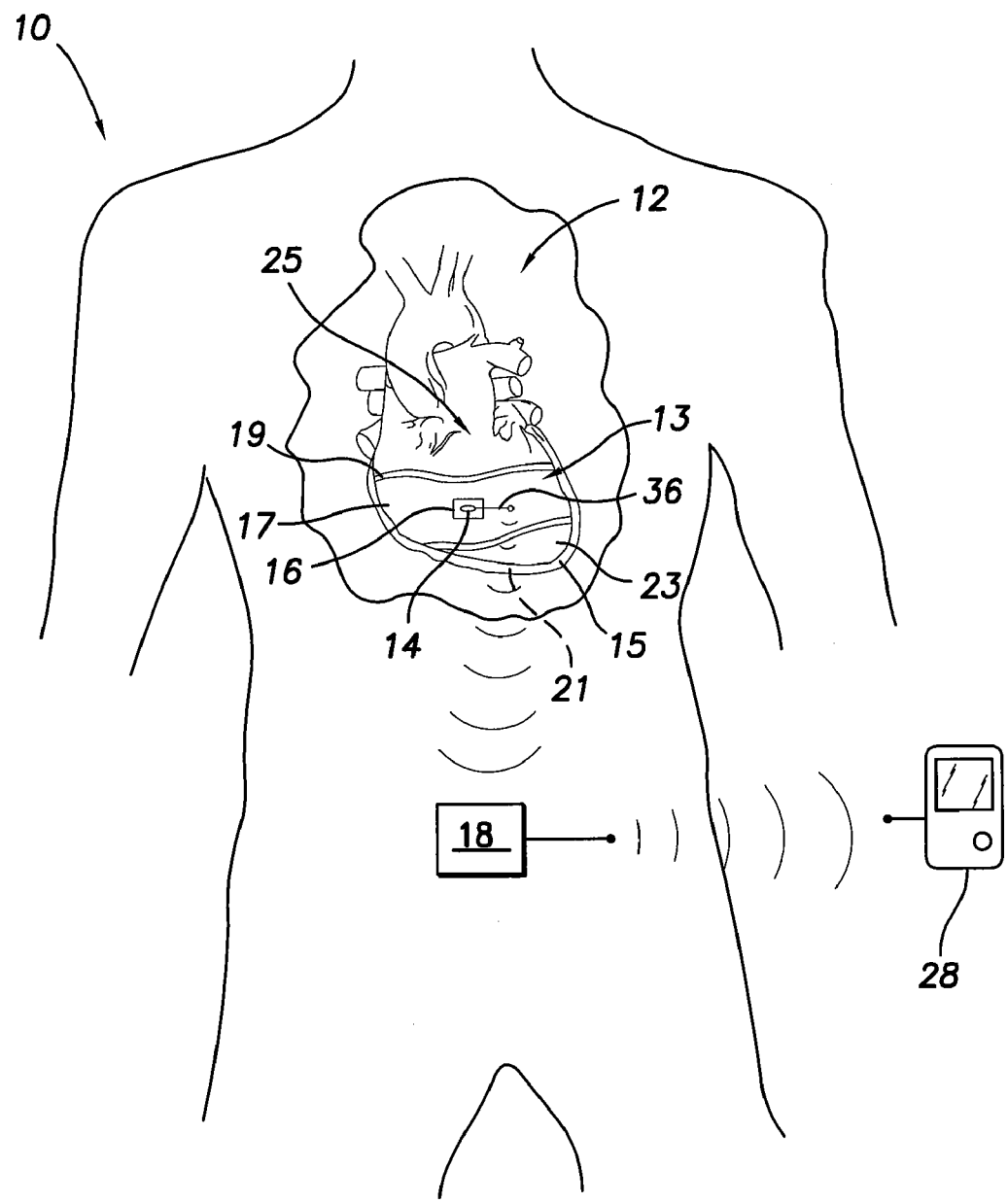
FIG. 2 illustrates the implantable sensor system shown in FIG. 1 positioned in accordance with an alternative embodiment of the present invention.

FIG. 2 illustrates the sensor system 10 positioned in accordance with an alternative embodiment of the present invention. Specifically, as shown in FIG. 2, the sensor element 14 is positioned within the pericardial space 13 in direct contact with the surface 17 of the serous pericardium 19 of the pericardium 15, as opposed to the epicardial surface 22 as shown in FIG. 1. Further, the sensor element 14 is electrically connected to the processing unit 18 using a radio-frequency (RF) transmitter 36 electrically connected to the sensor element 14, as opposed to the lead 26 (FIG. 1).

FIG. 3 illustrates a sensor element 14 in more detail. The sensor element 14 includes the body 20 extending between a pair of opposite end portions 38 and 40. In the exemplary embodiment of FIG. 3, the sensor body 20 includes a plurality of layers 41 of piezopolymer that are sandwiched together. Alternatively, the sensor body 20 includes only one layer of piezopolymer. A surface 35 of one of the layers 41a of the body 20 may optionally be at least partially coated with one or more layers of any suitable electrically conductive material 37, such as, but not limited to, silver and/or another electrical conductor. In the exemplary embodiment, the body 20 includes two layers of the electrically conductive material 37 on the surface 35. In some embodiments, a surface 43 of another of the layers 41b may also be at least partially coated with one or more layers of any suitable electrically conductive material.

A pair of electrodes 42 and 44 are attached to the proximate end portion 40 of the body 20 on an exposed surface 39 of the outermost layer of the electrically conductive material 37. As described above, the sensor body 20 is fabricated from a piezopolymer, such as, but not limited to, PVDF. In the exemplary embodiment of FIG. 3, the sensor body 20 is substantially longer in the longitudinal direction along length L, as compared to the width W that extends in the transverse direction. For example, the sensor body 20 may have a length L that is 3 or more times the width W. As a further option, the length L may be ten or more times the width W. The piezopolymer material of the sensor body 20 is a generally flexible material that enables the sensor element 14 to bend when in contact with bodily tissue and/or fluid that is in motion.

The plurality of layers 41 may facilitate increasing a measurement sensitivity of the sensor body 20 as compared with only one layer. For example, each layer 41 may generate the same voltage output for the same amount of motion such that the overall voltage output is N times larger (where N is the number of layers 41). The layers 41 may be attached together using any suitable method, process, structure, means, and/or the like, such as, but not limited to, using heat, compression, and/or adhesive, such as, but not limited to, and electrically conductive adhesive, such as, but not limited to, silver epoxy. Although four layers 41 are shown, the sensor body 20 may include any number of layers 41.

Each layer 41 of the sensor body 20 may be fabricated, for example, by repeatedly pulling the piezopolymer material along the molecular chain direction of the material, whether the layers 41 are pulled together or separately. During pulling thereof, each layer 41 is electrically polarized. After such a fabrication process, the sensor body 20 generates the strongest signals along the molecular chain direction, e.g., along the longitudinal axis denoted by the length L of the sensor body 20. As discussed above, as the sensor body 20 bends along the longitudinal axis or the length L, an electrical charge is generated within the body 20, which collects at the electrodes 42 and 44. An output voltage of the electrical charge across the pair of electrodes 42 and 44 is proportional to the bending moment and the rate of bending of the sensor element 14. For example, the charge collected at the electrodes 42 and 44 may increase linearly in proportion to the amount that the sensor element 14 is bent along the longitudinal axis.

Optionally, the charge at the electrodes 42 and 44 may increase non-linearly, but in a known relation, in proportion to the amount that the sensor element 14 is bent. For example, the non-linear proportion may be exponential, a second or third order polynomial, and the like. The charge at the electrodes 42 and 44 is measured as a voltage potential and used to determine motion properties of the fluid and/or tissue whose motion caused the sensor element 14 to bend. The electrodes 42 and 44 are electrical connected to either the lead 26 (FIG. 1) or the RF transmitter 36 (FIG. 2), for example using leads 46 and 48, to provide the electrical connection between the sensor element 14 and the processing unit 18 (FIG. 1).

The sensor body 20 may have any suitable size, shape, and/or number of layers 41 that enables the sensor element 14 to function as described herein. The output voltage across the pair of electrodes 42 and 44 is proportional to the amount of surface area of the sensor body 20 that is stressed in the direction of the length L, such that the larger the surface area, the greater the charge, voltage, and signal strength. The size, shape, and/or number of layers 41 of the sensor body 20 may be selected to provide a desired voltage or signal strength. Although the sensor body 20 may have many other suitable shapes, in the exemplary embodiment shown in FIG. 3, the sensor body 20 is an elongated beam having a generally rectangular shape and cross section. Other suitable shapes of the sensor body include, but are not limited to, elliptical, square and/or tubular shapes. A shape that is elongate about the molecular chain direction, such as, but not limited to the elongate beam 20 shown in FIG. 3, may facilitate an increased surface area that is stressed during bending, and therefore facilitate increased signal strength. Exemplary sizes for an elongate beam that may be suitable for implantation adjacent, on, and/or within the heart 12 (FIGS. 1 and 2) include, but are not limited to, a length L of between approximately 3 mm and approximately 11 mm, a width W of between approximately 1 mm and approximately 5 mm, and a thickness T of between approximately 5 μm and approximately 100 μm. By way of example, a sensor body having a length of approximately 10 mm, a width of approximately 4 mm, and a thickness of approximately 25 μm may generate in the order of hundreds of millivolts to ones of Volts. The net voltage across the pair of electrodes 42 and 44 generated by the bending of the body 20 can be represented by the piezocoefficient $d_{31}$.

As the piezopolymer material of the sensor body 20 generates signals primarily along the molecular chain direction (along the length L), the sensor element 14 has a relatively small value (e.g., approximately zero) of the piezocoefficient $d_{33}$, which represents the ratio of the pressure to the generated voltage of the piezopolymer material of the sensor body 20. The smaller $d_{33}$ coefficient of the piezopolymer material of the sensor body 20 reduces an amount of noise signals within the measurement signals of the sensor element 14, for example caused by hydrostatic pressure. Accordingly, use of the piezopolymer material of the sensor body 20 may result in higher signal clarity when the sensor body is used to measure motion. Although the piezopolymer material of the sensor body 20 has a relatively small $d_{31}$ value, the piezopolymer material of the sensor body is generally flexible. The piezopolymer material of the sensor body 20 will therefore readily bend, which may generate a signal strength representing bending along the length L of the sensor body that is quite large. By way of example, the piezopolymer material of the sensor body 20 may produce a signal strength that represents bending along the length L of the sensor body that is in the order of ones of millivolts to tens of Volts.

Because the measurement signals of the sensor element 14 are generated by bending of the sensor body 20, the sensor element does not require an external power source for measuring motion. Moreover, the piezopolymer material of the sensor body 20 is generally biocompatible, and therefore is generally suitable for implantation within the human body and may not require hermetic sealing.

The electrodes 42 and 44 may each have any suitable position on the sensor body 20 that enables them to function as described herein. Generally, as long as the electrodes 42 and 44 are spaced apart from one another such that the electrodes 42 and 44 are not electrically connected together, the position of the electrodes 42 and 44 may not affect the signal strength or more specifically the amount of voltage potential across the electrodes 42 and 44. In the exemplary embodiment of FIG. 3, the electrodes 42 and 44 are positioned adjacent each other on the same side portion 50 and the same end portion 40 of the sensor body 20.

The electrodes 42 and 44 may be fabricated using any suitable electrically conductive material(s) that enables them to function as described herein, such as, but not limited to silver, aluminum, gold, copper, nickel, palladium, platinum, rhodium, rhenium, tin, other metallic conductors, and/or the like. In the exemplary embodiments, each of the electrodes 42 and 44 is formed by a layer of silver that is print-coated on the sensor body 20. In the exemplary embodiment, the electrodes 42 and 44, and/or any connection between the electrodes 42 and 44 and the lead 26 and/or the transmitter 36, are be coated with any suitable insulating material (not shown in FIG. 3).

Figure 4:
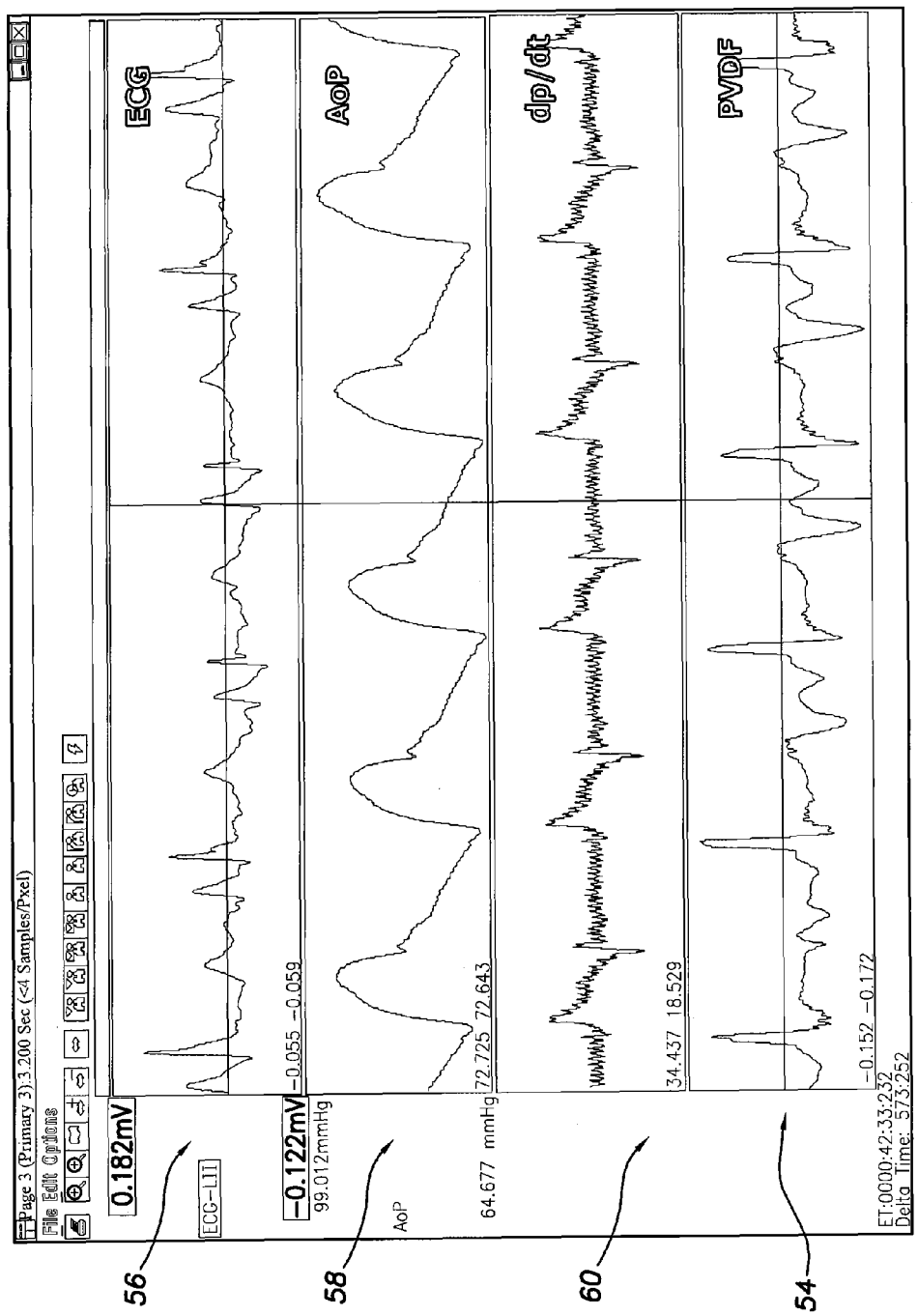
FIG. 4 illustrates an exemplary measurement signal generated by the implantable sensor system shown in FIG. 2 in response to motion of a heart.

FIG. 4 illustrates an exemplary measured signal 54 generated by the sensor element 14 in response to motion. In the embodiment represented in FIG. 4, the sensor element 14 has been implanted and positioned within the pericardial space 13 (FIG. 2) adjacent the left ventricle 25 in direct contact with the surface 17 of the serous pericardium 19 of the pericardium 15. The sensor element 14 has been orientated such that the length L of the sensor body 20 is approximately parallel to the short axis of the heart (e.g., as shown in FIG. 2). The sensor element 14 is thus used to measure the heart motion along the short axis. The measured signal 54 represents the motion of the left ventricle over time. Also shown are signals 56, 58, and 60, respectively, representing an electrocardiogram (ECG), the aortic pressure (AoP), and the derivative of the blood pressure (dp/dt) of the heart over the same time period.

FIGS. 5 and 6 illustrate sensor elements 114 and 214, respectively, having exemplary alternative shapes and exemplary alternative electrode positions than the previously described and/or illustrated sensor element 14. Specifically, FIG. 5 illustrates the sensor element 114 having electrodes 142 and 144 attached on opposite side portions 150 and 152 of a body 120 of the sensor element 114. The sensor body 120 has a generally square shape in contrast to the elongate beam of the sensor body 20 (FIG. 3). Although shown as having only one layer of piezopolymer, the sensor body 120 may alternatively include two or more layers of piezopolymer. FIG. 6 illustrates the sensor element 214 having the electrodes 242 and 244 attached on opposite ends 238 and 240 of a body 220 of the sensor element 214. The sensor body 220 has a generally elongate tubular shape in contrast to the elongate beam of the sensor body 20 (FIG. 3). Although shown as cylindrical, the tubular shape of the sensor body 220 may alternatively be a tubular shape that is not generally cylindrical (e.g., a square tube). Although shown as having only one layer of piezopolymer, the sensor body 220 may alternatively include two or more layers of piezopolymer.

Figure 7:
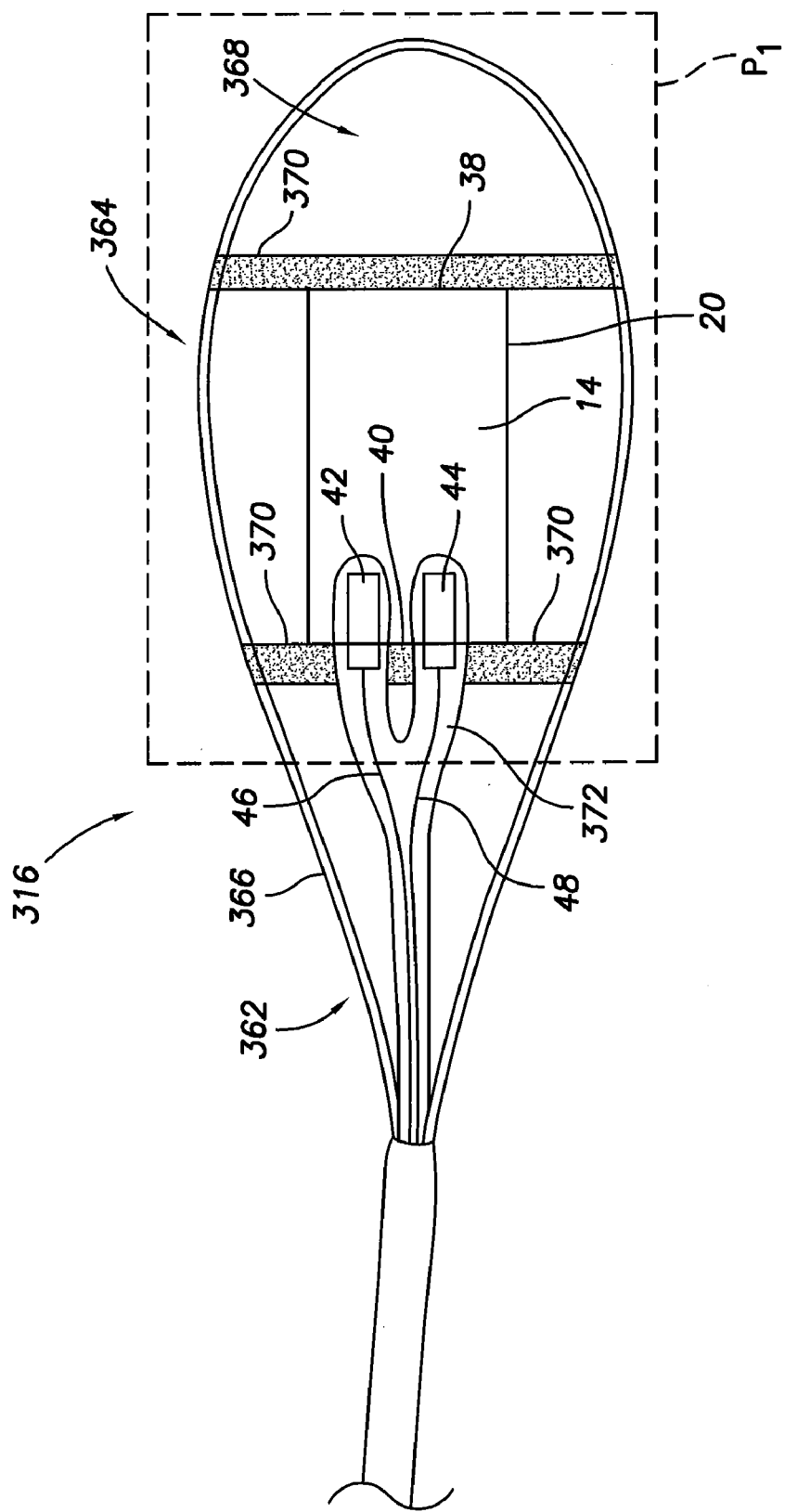
FIG. 7 illustrates an attachment device of the system shown in FIGS. 1 and 2 formed in accordance with an embodiment of the present invention.

FIG. 7 illustrates an attachment device 316 formed in accordance with an embodiment of the present invention. The attachment device 316 forms the end portion 362 of a lead (e.g., the lead 26 shown in FIG. 1). Specifically, the attachment device 316 includes a loop-shaped portion 364 that is formed by a cable 366 of the lead. The sensor element 14 is held within a space 368 bounded by the loop-shaped portion 364. The sensor element 14 and the loop-shaped portion 364 generally lie in a plane $P_1$.

The sensor element 14 may be held within the loop-shaped portion 364 using any suitable structure, method, configuration, arrangement, orientation, and/or means that enable the sensor element 14 to function as described herein. In the exemplary embodiment of FIG. 7, the sensor element 14 is held within the loop-shaped portion 364 using supports 370. Although the supports 370 may have any suitable configuration and/or arrangement, in the exemplary embodiment the supports attached to the lead cable 366 and extending across the space 368 bounded by the loop-shaped portion 364 are attached to the sensor body 20 at each of the ends 38 and 40 thereof.

The supports 370 may be fabricated from any suitable material(s) that are capable of securely holding the sensor body 20 in the position shown in FIG. 7, such as, but not limited to, silicone, polyurethane, Hemoflex®, and/or an adhesive, such as, but not limited to, a medical grade adhesive, such as, but not limited to, Med A (commercially available from Dow Chemical of Midlands, Mich.). An insulating material 372 encapsulates the electrodes 42 and 44 and the respective leads 46 and 48 of the electrodes 42 and 44 to insulate the electrical connections of the sensor element 14. The cable 366 may be fabricated from any suitable material(s) that enable the attachment device 316 to function as described herein. Optionally, the lead is a lead of another system (not shown), such as, but not limited to a pulse generator, a pacemaker, an implantable cardioverter defibrillator, a defibrillator, a therapy delivery module that paces and/or provides electrical stimulation to the heart 12, and/or the like.

The attachment device 316 may be positioned adjacent, on, and/or within the heart 12 (FIG. 1) (or other bodily tissue and/or fluid) by positioning the end portion 362 of the lead at the desired location of the heart 12 such that the sensor element 14 is positioned at the desired location and in the desired orientation. Because the loop-shaped portion 364 is connected to the lead cable 366, the sensing element 14 will remain at the desired location and in the desired orientation as long as the lead cable 366 is not moved. Frictional forces between the sensor body 20 and/or the lead cable 366 and adjacent surfaces with which the sensor body and/or the lead cable are in contact may also facilitate securely holding the sensor element 14 at the desired location and in the desired orientation. For example, frictional forces between the sensor body and a surface of the heart 12 or a surface of the pericardium 15 (FIG. 2) may facilitate holding the sensor element 14 in direct contact with the surface. When the sensor element is orientated to be within a flow path of blood within the heart 12, frictional forces between lead cables 366 and surfaces defining the blood flow path may facilitate securely holding the sensor element within the flow path.

Figure 8:
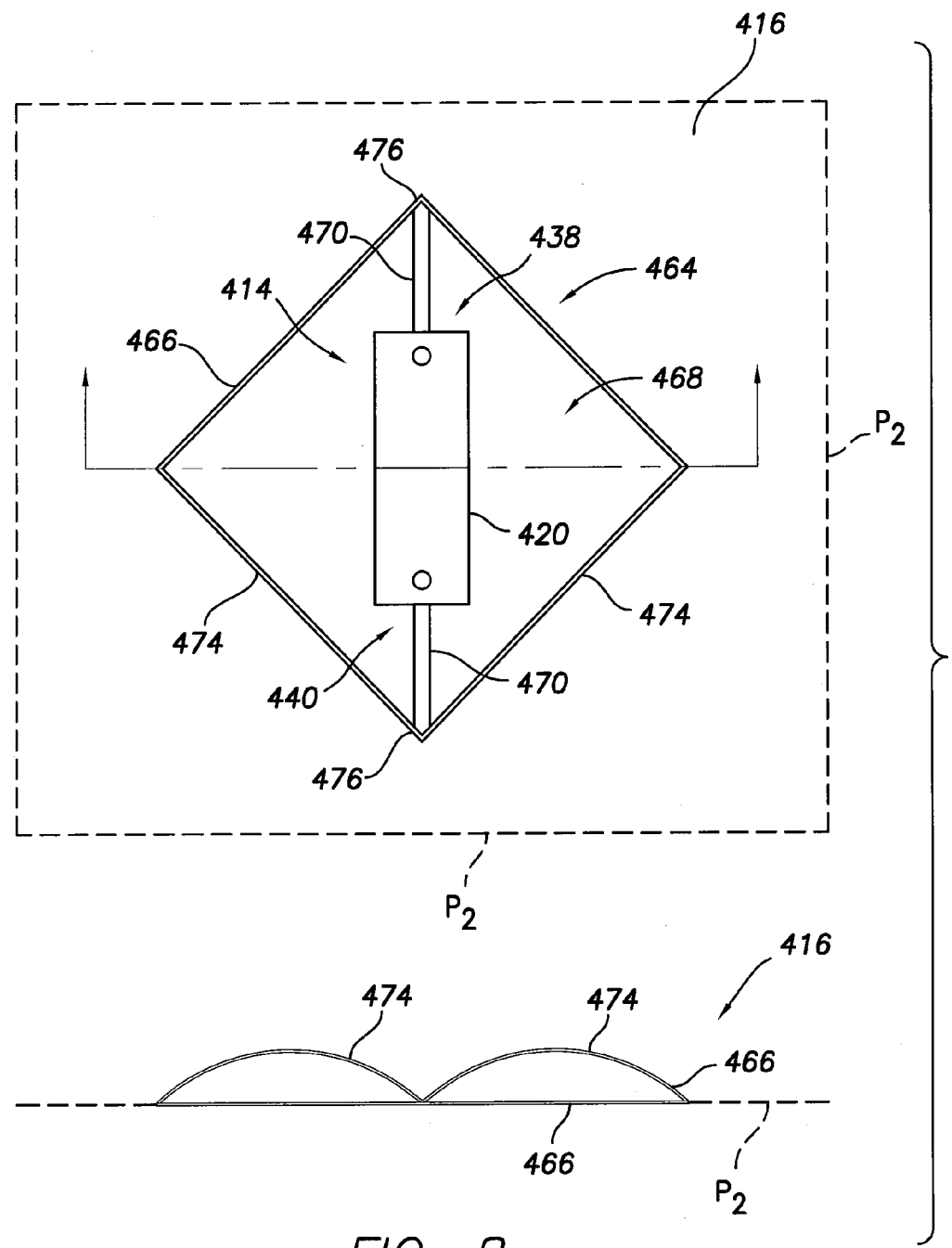
FIG. 8 illustrates an attachment device formed in accordance with an alternative embodiment of the present invention.

FIG. 8 illustrates an attachment device 416 formed in accordance with an embodiment of the present invention. The attachment device 416 includes a diamond-shaped portion 464 that is formed by a cable 466. A sensor element 414 is held within a space 468 bounded by the diamond-shaped portion 464. The sensor element 414 and the diamond-shaped portion 464 generally lie in a plane $P_2$. However, one or more cable portions 474 of the diamond-shaped portion 464 may be bowed outwardly such that the portions 474 extend outwardly away from the plane $P_2$. Although two portions 474 are shown as extending outwardly in generally the same direction, any number of portions 474 may be bowed outwardly, with each portion 474 extending outwardly in any direction relative to the plane $P_2$ and/or the other portions. For example, two portions 474 may extend outwardly from the plane $P_2$ in generally opposite directions.

The sensor element 414 may be held within the diamond-shaped portion 464 using any suitable structure, configuration, arrangement, orientation, method, and/or means that enable the sensor element 414 to function as described herein. In the exemplary embodiment of FIG. 8, the sensor element 414 is held within the diamond-shaped portion 464 using supports 470. Although the supports 470 may have any suitable configuration and/or arrangement, in the exemplary embodiment a pair of supports 470 are attached to opposite ends 438 and 440 of the sensor body 420, where each support 470 extends away from the sensor body 420 to attach to an opposite corner 476 of the diamond-shaped portion 464.

The attachment device 416 may be positioned adjacent, on, and/or within the heart 12 (FIG. 1) (or other bodily tissue and/or fluid) by positioning the diamond-shaped portion 464 at the desired location of the heart 12 such that the sensor element 414 is positioned at the desired location and in the desired orientation. The bowed portions 474 facilitate securely holding the sensor element 414 at the desired location and in the desired orientation by providing spring force against adjacent surfaces. For example, when the sensor element 414 and the attachment device 416 are positioned within the pericardial space, the bowed portions 474 may exert a spring force against the epicardial surface 22 (FIG. 1) of the heart 12 and/or against a surface of the pericardium 15 (FIG. 2). Frictional forces between the sensor body 420 and/or the cable 466 and adjacent surfaces with which the sensor body 420 and/or the cable 466 are in contact may also facilitate securely holding the sensor element 414 at the desired location and in the desired orientation.

Figure 9:
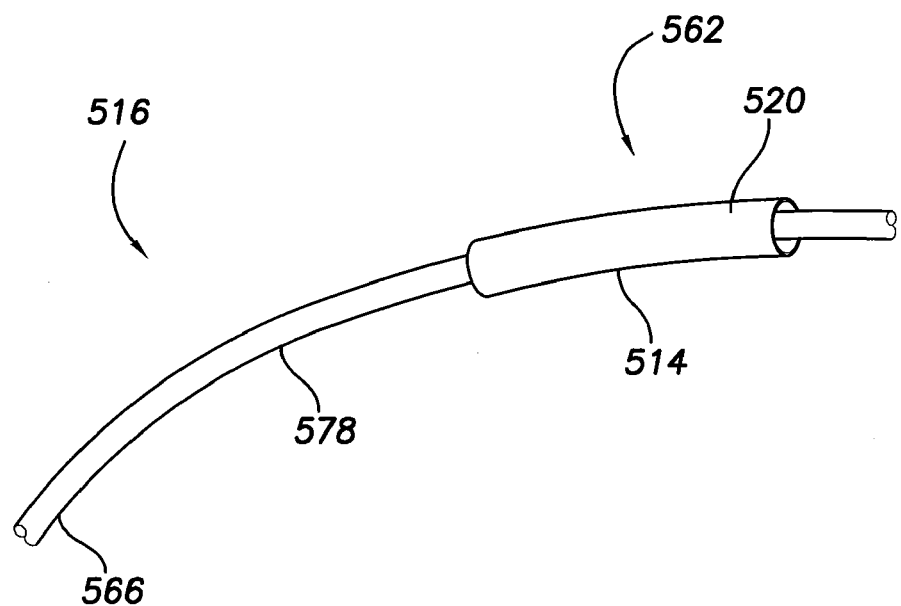
FIG. 9 illustrates an attachment device formed in accordance with another alternative embodiment of the present invention.

FIG. 9 illustrates an attachment device 516 formed in accordance with an embodiment of the present invention. The attachment device 516 is the end portion 562 of a lead (e.g., the lead 26 shown in FIG. 1). Specifically, the attachment device 516 includes a cable 566 of the lead. The sensor body 520 is received on an exterior surface 578 of the cable 566 such that the sensor body 520 may completely surround a portion of the cable 566. Although the cable 566 may have any suitable shape, and the sensor body 520 may have any suitable shape, in the exemplary embodiment shown in FIG. 9 the cable 566 and the sensor body 520 each include a generally cylindrical shape. Although the body 520 of the sensor element 514 has a shape that is complimentary with the cable 566, alternatively the sensor body 520 and the cable 566 may have different shapes.

Figure 10:
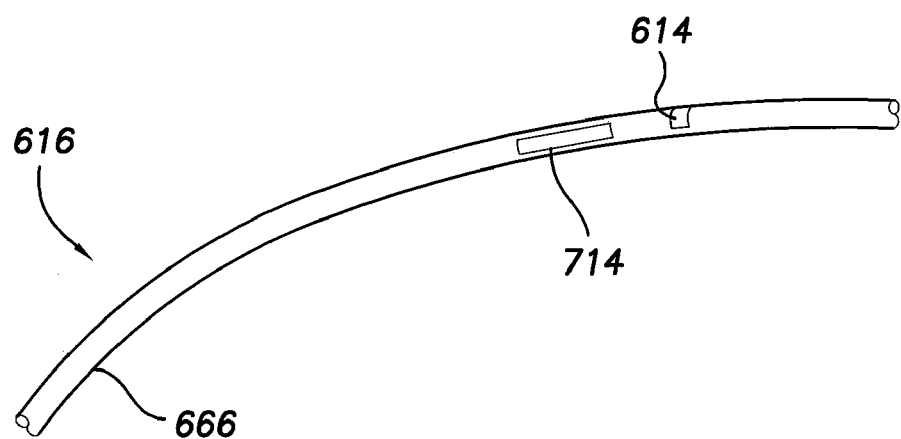
FIG. 10 illustrates an attachment device formed in accordance with another alternative embodiment of the present invention.

FIG. 10 illustrates an attachment device 616 formed in accordance with an embodiment of the present invention. The attachment device 616 is similar to the attachment device 516 shown in FIG. 9 except that the sensor element 614 only partially surrounds the cable 666. Moreover, the cable 666 includes another sensor element 714 that is orientated approximately perpendicular to the sensor element 614 (e.g., for measuring motion of both the short axis and the long axis of the heart 12). Although the sensor elements 614 and 714 are shown as being held by the same attachment device 616, the sensor elements 614 and 714 may alternatively be held by different attachment devices.

Figure 11:
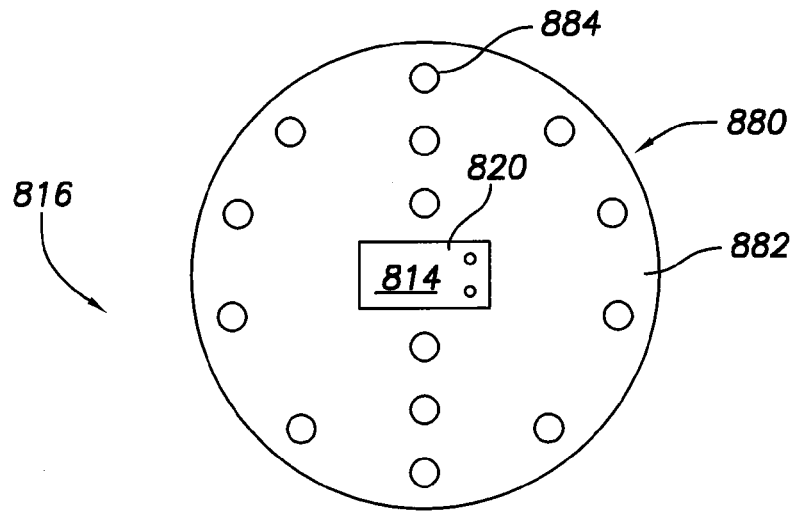
FIG. 11 illustrates an attachment device formed in accordance with another alternative embodiment of the present invention.

FIG. 11 illustrates an attachment device 816 formed in accordance with an embodiment of the present invention. The attachment device 816 includes a patch 880 having a body 882 configured to be attached to bodily tissue. The sensor element 814 may be held by the patch 880 using any suitable structure, method, configuration, orientation, arrangement, and/or means. For example, the sensor element 814 may be attached to the patch body 882 using an adhesive, may be attached to the patch body 882 by molding, crimping, welding, and/or suturing, and/or the sensor element 814 may be embedded between two layers of the patch body.

The patch 880 may include one or a plurality of layers, whether such layers are made from the same or different materials. The patch 880 may be fabricated from any suitable material(s), such as, but not limited to, polyester, polypropylene, polytetrafluoroethylene, polyurethane, silicone, silicone rubber, and/or the like. The type of material selected may depend on factors such as the materials softness, stiffness, pliability, flexibility, useful life, biocompatibility, adhesiveness, ability to allow tissue ingrowth, and/or other characteristics.

The attachment device 816 may be positioned adjacent, on, and/or within the heart 12 (FIGS. 1 and 2) (or other bodily tissue and/or fluid) by positioning the patch 880 at the desired location of the heart 12 such that the sensor element 814 is positioned at the desired location and in the desired orientation. The patch 880 may include a plurality of pores 884 extending within the body 882 to increase the adherence and compliance of the patch 880 to a surface of the heart 12 by allowing tissue to grow into or through the pores 884. The tissue ingrowth helps stabilize the patch 880 to the surface of the heart 12. The pores 884 are sufficiently sized and shaped to allow an adequate amount of tissue ingrowth to enhance the adherence of the patch 880 to the surface of the heart 12. Optionally, the pores 884 may be cylindrical; however, the shape of each of the pores 884 is not limited to a cylindrical shape. Optionally, the pores 884 may have angled walls. In addition or alternative to the pores 884, frictional forces between the sensor body 820 and/or the patch body 882 and adjacent surfaces with which the sensor body 820 and/or the patch body 882 are in contact may facilitate securely holding the sensor element 814 at the desired location and in the desired orientation. Another additional or alternative example includes suturing the patch body 882 to a surface of the heart 12 (or other bodily tissue and/or fluid).

Figure 12:
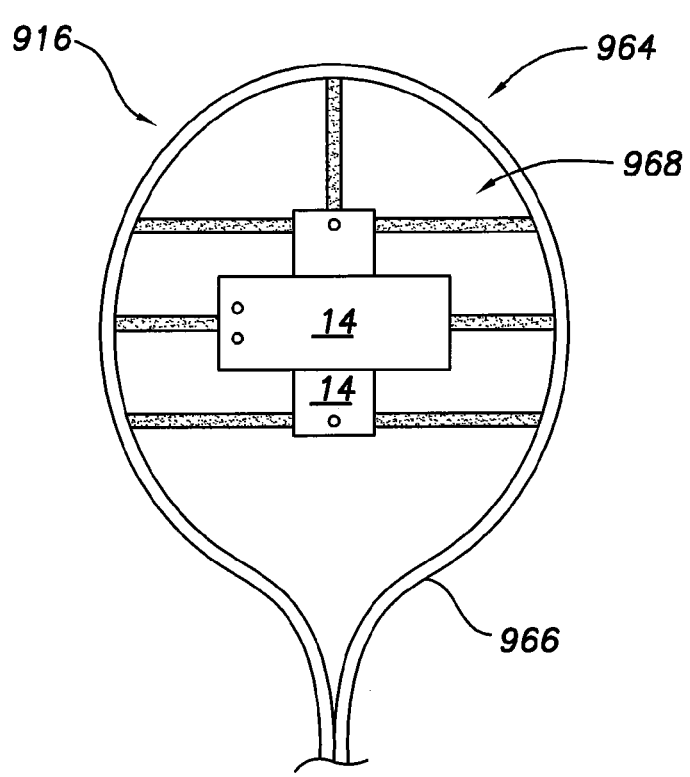
FIG. 12 illustrates an attachment device formed in accordance with another alternative embodiment of the present invention.

FIG. 12 illustrates an attachment device 916 formed in accordance with an embodiment of the present invention. The attachment device 916 includes a loop-shaped portion 964 that is formed by a cable 966. A pair of the sensor elements 14 are held within a space 968 bounded by the loop-shaped portion 964. The sensor elements 14 are held by the attachment device 916 such that the sensor elements are orientated approximately perpendicular to each other (e.g., for measuring motion of both the short axis and the long axis of the heart 12 (FIGS. 1 and 2)). Although the pair of sensor elements 14 are shown as being held by the same attachment device 916, the pair of sensor elements 14 may alternatively be held by different attachment devices.

Figure 13:
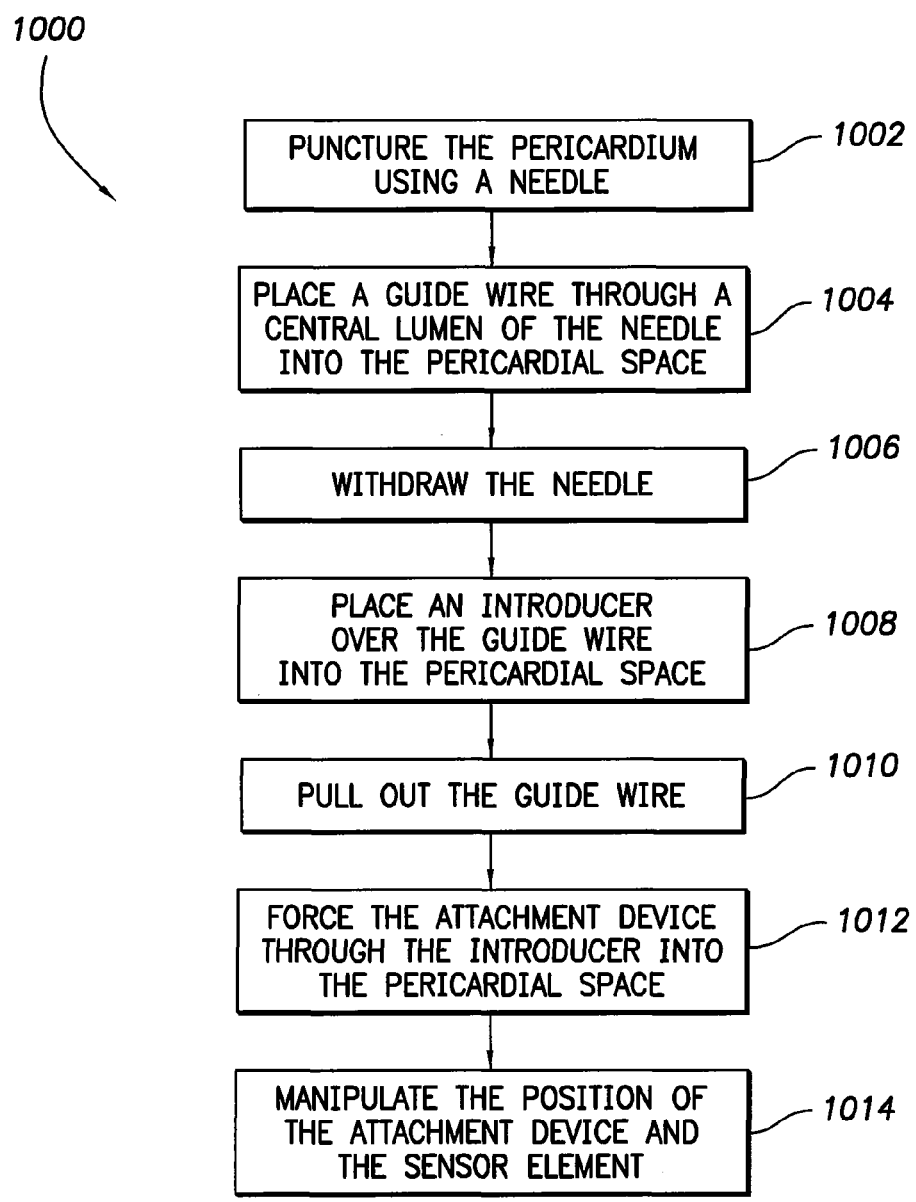
FIG. 13 illustrates an exemplary embodiment of a method for positioning a sensor element.

The sensor elements described and/or illustrated herein may be placed into the positions described and/or illustrated herein using any suitable method, structure, and/or means. For example, FIG. 13 illustrates an exemplary embodiment of a method 1000 for positioning a sensor element. When positioning a sensor element within the pericardial space (e.g., positioning the sensor element 14 (FIG. 2) within the pericardial space 13 in direct contact with the surface 17 of the serous pericardium 19 of the pericardium 15) a needle (not shown, e.g., a Touhy needle) may be used to puncture 1002 the pericardium 15 (e.g., at the subxiphoid) and gain access to the pericardial space 13. A guide wire (not shown) is placed 1004 through a central lumen of the needle into the pericardial space 13. The needle is then withdrawn 1006 and an introducer (not shown) is placed 1008 over the guide wire into the pericardial space 13. The guide wire is then pulled out 1010 and the attachment device, including the sensor element and any leads associated with the attachment device and/or the sensor element, is then forced 1012 through the introducer into the pericardial space 13. A stylet (not shown) can then be used to manipulate 1014 the position of the attachment device and thereby the sensor element.

The embodiments described and/or illustrated herein provide an implantable piezoelectric sensor with improved signal clarity over at least some known piezoelectric sensors. The embodiments described and/or illustrated herein also provide an implantable sensor that is biocompatible and does not require an external power source and/or hermetic sealing.

Exemplary embodiments are described and/or illustrated herein in detail. The embodiments are not limited to the specific embodiments described herein, but rather, components and/or steps of each embodiment may be utilized independently and separately from other components and/or steps described herein. Each component, and/or each step of one embodiment, can also be used in combination with other components and/or steps of other embodiments. For example, although specific sensor elements are described and/or illustrated with specific attachment devices, each described and/or illustrated sensor element may be used with any of the described and/or illustrated attachment devices as is appropriate.

When introducing elements/components/etc. described and/or illustrated herein, the articles "a", "an", "the", "said", and "at least one" are intended to mean that there are one or more of the element(s)/component(s)/etc. The terms "comprising", "including" and "having" are intended to be inclusive and mean that there may be additional element(s)/component(s)/etc. other than the listed element(s)/component(s)/etc. Moreover, the terms "first," "second," and "third," etc. in the claims are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

While the invention has been described in terms of various specific embodiments, those skilled in the art will recognize that the invention can be practiced with modification within the spirit and scope of the claims.

What is claimed is:

1. An implantable lead comprising:
a first piezopolymer sensor element;
a second piezopolymer sensor element; and
an attachment device configured to hold the first piezopolymer sensor element and the second piezopolymer sensor element in direct contact with at least one of a bodily fluid and bodily tissue such that the piezopolymer sensor elements bend in response to motion of the at least one of bodily fluid and bodily tissue;
wherein the first piezopolymer sensor element and the second piezopolymer sensor element are arranged to at least partially overlap each other and are held in approximately perpendicular orientation with respect to one another.

2. The lead of claim 1 wherein the first and second sensor elements comprise polyvinylidene fluoride (PVDF).

3. The lead of claim 1 wherein the attachment device comprises a generally cylindrical cable, and the first and second sensor elements are on an exterior surface of the cable such that the first and second sensor elements at least partially surrounds a portion of the cable.

4. The lead of claim 1 wherein the attachment device comprises a patch having a body portion configured to be attached to a surface of the heart.

5. The lead of claim 1 wherein the attachment device is configured for endocardial placement.

6. The lead of claim 1 wherein the attachment device is configured for pericardial placement.

7. The lead of claim 1 further comprising two pairs of electrodes, one pair attached to each of the first and second sensor elements, the electrodes configured to collect an electrical charge generated within the sensor elements due to the bending of the sensor elements.

8. The lead of claim 1 wherein the first and second sensor elements and the attachment device lie in a common plane.

9. An implantable lead comprising:
a first piezopolymer sensor element;
a second piezopolymer sensor element; and
an attachment device configured to hold the first piezopolymer sensor element and the second piezopolymer sensor element in direct contact with at least one of a bodily fluid and bodily tissue such that the piezopolymer sensor elements bend in response to motion of the at least one of bodily fluid and bodily tissue;
wherein the first piezopolymer sensor element and the second piezopolymer sensor element are held in approximately perpendicular orientation with respect to one another;
wherein the attachment device comprises a cable defining an at least partially loop-shaped portion having an open space bounded thereby; and the first and second sensor elements are held within the open space.

10. The lead of claim 9 wherein the loop-shaped portion defines an at least partially diamond-shaped portion.

11. The lead of claim 10 wherein the diamond-shaped portion comprises one or more cable portions that lie in a common plane with the sensor element and one or more cable portions that bow outwardly from the common plane.

12. The lead of claim 9 further comprising a plurality of supports extending from the cable across the open space, wherein the supports attach to the first and second sensor elements to hold the sensor elements in place within the open space.

* * * * *